United States Patent
Suzuki et al.

(10) Patent No.: US 9,615,833 B2
(45) Date of Patent: Apr. 11, 2017

(54) METHOD FOR PRODUCING IN-VIVO INDWELLING MEMBER

(71) Applicant: KANEKA CORPORATION, Osaka-shi, Osaka (JP)

(72) Inventors: Shohei Suzuki, Settsu (JP); Tamotsu Shimada, Settsu (JP); Hironori Takata, Settsu (JP)

(73) Assignee: KANEKA CORPORATION, Osaka-shi (JP)

( * ) Notice: Subject to any disclaimer, the term of this patent is extended or adjusted under 35 U.S.C. 154(b) by 9 days.

(21) Appl. No.: 14/410,460

(22) PCT Filed: Jun. 3, 2013

(86) PCT No.: PCT/JP2013/065377
§ 371 (c)(1),
(2) Date: Dec. 22, 2014

(87) PCT Pub. No.: WO2014/002696
PCT Pub. Date: Jan. 3, 2014

(65) Prior Publication Data
US 2015/0289881 A1    Oct. 15, 2015

(30) Foreign Application Priority Data

Jun. 29, 2012 (JP) ................... 2012-146343

(51) Int. Cl.
*A61B 17/12* (2006.01)
*A61B 17/00* (2006.01)

(52) U.S. Cl.
CPC .. *A61B 17/12145* (2013.01); *A61B 17/12031* (2013.01); *A61B 17/12113* (2013.01);
(Continued)

(58) Field of Classification Search
CPC ........ A61B 17/12145; A61B 17/12031; A61B 17/12113; A61B 17/00526; B21F 45/008;
(Continued)

(56) References Cited

U.S. PATENT DOCUMENTS 5,639,277 A * 6/1997 Mariant ........... A61B 17/12022
606/191
5,649,949 A * 7/1997 Wallace ........... A61B 17/12022
600/200

(Continued)

FOREIGN PATENT DOCUMENTS

| EP | 0 765 636 A2 | 4/1997 |
| JP | 3024071 B2 | 3/2000 |

OTHER PUBLICATIONS

International Search Report, issued in PCT/JP2013/065377, dated Jul. 16, 2013.

*Primary Examiner* — Debra Sullivan
(74) *Attorney, Agent, or Firm* — Birch, Stewart, Kolasch & Birch, LLP

(57) ABSTRACT

A method for producing an in-vivo indwelling member includes a step of winding a metal wire (1) to form a primary coil (2-4), a step of giving the primary coil (2-4) a shape to form a secondary coil (10-19), and a step of inserting the secondary coil (10-19) into an inner hollow section (43) of a shaping mold (40). The secondary coil (10-19) includes different patterns such as a helical shape (20, 22-25, 29, 61, 63-65), a linear shape (21, 26, 28), and a circular arc shape (27, 50-53, 60, 62). When the secondary coil (10-19) is pushed into the inner hollow section (43), the secondary coil (10-19) makes contact with the inner wall surface of the inner hollow section (43), and a portion between different patterns is randomly curved. Accordingly, the in-vivo indwelling member has a three-dimensional structure that corresponds to the shape of the inner hollow section (43).

(Continued)

The in-vivo indwelling member is less likely to deviate from the inside of an aneurysm when released into the aneurysm.

11 Claims, 10 Drawing Sheets

(52) U.S. Cl.
CPC ............... *A61B 2017/00526* (2013.01); *A61B 2017/00867* (2013.01)

(58) Field of Classification Search
CPC ...... B21F 3/04; B21F 3/12; A61F 2/88; A61F 2/94
See application file for complete search history.

(56) References Cited

U.S. PATENT DOCUMENTS

| | | | |
|---|---|---|---|
| 5,749,891 A * | 5/1998 | Ken | A61B 17/12022 606/108 |
| 5,911,731 A | 6/1999 | Pham et al. | |
| 6,322,576 B1 | 11/2001 | Wallace et al. | |
| 7,485,123 B2 * | 2/2009 | Porter | A61B 17/12022 606/113 |
| 2005/0192618 A1 | 9/2005 | Porter | |
| 2006/0184195 A1 | 8/2006 | Schaefer et al. | |
| 2007/0175536 A1 * | 8/2007 | Monetti | A61B 17/12022 140/102.5 |
| 2013/0066359 A1 * | 3/2013 | Murphy | A61B 17/12113 606/200 |

* cited by examiner

METHOD FOR PRODUCING IN-VIVO INDWELLING MEMBER

TECHNICAL FIELD

The present invention relates to a method for producing an in-vivo indwelling member, and particularly to a method for producing an in-vivo indwelling member that is deployed into a spherical shape or the like when being in use.

BACKGROUND ART

In order to treat a bump such as an aneurysm generated in a blood vessel such as an artery, a medical instrument called a microcatheter which includes an elongated tube having a small outer diameter and an inner cavity is first allowed to pass through the blood vessel and guided into the bump. Then, an in-vivo indwelling member is inserted into the bump through the inner cavity of the microcatheter and indwelled therein. Accordingly, the in-vivo indwelling member becomes a physical obstacle against blood flow and a thrombus is formed around the in-vivo indwelling member. As a result, it is possible to reduce the risk of rupture of the bump such as an aneurysm.

Generally, an in-vivo indwelling member is composed of a metal coil. The metal coil is composed of a secondary coil (see FIG. 3, for example) which is formed into a generally linear shape as a whole by further helically winding a primary coil (see FIG. 1(a), for example) which is obtained by forming a metal wire into a coil shape. When the in-vivo indwelling member which is composed of the secondary coil is guided to a bump such as an aneurysm, the form of the secondary coil is released inside a microcatheter and the in-vivo indwelling member is then guided in a linear form. Then, when the in-vivo indwelling member is released from the microcatheter inside the bump, the shape thereof returns to the form of the secondary coil so that the in-vivo indwelling member can remain inside the bump.

On the other hand, a bump has a various shapes such as a spherical shape, an elliptical spherical shape, a bifurcated bump shape, and a shape in which another blood vessel branches from a bump. Among these shapes, a type called a wide neck aneurysm in which the boundary with a parent blood vessel is wide relative to the diameter of the aneurysm has the following problem. Specifically, when indwelling an in-vivo indwelling member that is composed of a metal coil, for example, a general secondary coil having a helical shape as illustrated in FIG. 3, tensile force for the secondary coil to remain inside the aneurysm is weak due to a wide neck opening. Therefore, the secondary coil jumps out into the parent blood vessel and is caused to flow to the periphery by the blood flow, which may cause a serious risk.

Therefore, it is known that, when an in-vivo indwelling member released from a microcatheter has a three-dimensional structure that differs from the secondary coil having a generally linear shape as a whole as described above with respect to such a wide neck aneurysm, the in-vivo indwelling member can firmly remain inside a bump along the shape of the bump, and the risk of deviation of the in-vivo indwelling member is therefore reduced.

There have been proposed various in-vivo indwelling members having a three-dimensional structure as described above and various producing methods thereof. For example, Patent Document 1 describes a method in which a primary coil is wound around a spherical mandrel or inserted into a mold having a spherical inner hollow section to thereby form an in-vivo indwelling member having a spherical three-dimensional structure.

However, in the method described in Patent Document 1, although the in-vivo indwelling member that has a spherical three-dimensional structure as a whole is formed using the linear primary coil, it is difficult to maintain the form as it is and the shape thereof is therefore disadvantageously lost. Further, when inserting the primary coil into the mold having the spherical inner hollow section, the primary coil is inserted only along substantially the same trajectory inside the mold. Therefore, the primary coil is disadvantageously formed only into a shape wound to have a substantially constant outer diameter (for example, see FIG. 11 for reference).

CITATION LIST

Patent Document

Patent Document 1: Japanese Patent No. 3024071

SUMMARY OF INVENTION

Technical Problem

The present invention has been made in view of the above problems in a conventional technique, and an object thereof is to provide a method for producing an in-vivo indwelling member, the method being capable of easily producing an in-vivo indwelling member that can be more stably arranged inside an bump such as an aneurysm generated in a blood vessel such as an artery.

Solution to Problem

As a result of intensive studies to solve the above problems, the inventors of the present application have found out that, by using a secondary coil obtained by giving a primary coil a shape in which two or more predetermined patterns are continuously arranged, when inserting the secondary coil into a shaping mold having an inner hollow section, the secondary coil does not move along substantially the same trajectory inside the shaping mold, but can move in a random direction, thereby making it possible to produce an in-vivo indwelling member having a shape that substantially corresponds to the shape of the inner hollow section of the shaping mold, and thereby achieved the present invention.

An outline of the present invention is as follows.

(1) A method for producing an in-vivo indwelling member, the method including: a primary coil forming step of winding a metal wire to form a primary coil; a secondary coil forming step of giving the primary coil a shape in which two or more different patterns of two or more kinds are continuously arranged to form a secondary coil; and a step of inserting the secondary coil into a shaping mold having an inner hollow section.

(2) The method according to (1), wherein the different patterns of two or more kinds include at least one selected from a helical shape, a linear shape, a wavy shape, a curved shape, and a bent shape.

(3) The method according to (2), wherein the helical shape includes a helical shape having a varying outer diameter.

(4) The method according to (2) or (3), wherein the inner hollow section of the shaping mold is generally spherical, and a maximum width of the generally spherical inner hollow section is equal to or less than a minimum outer diameter of the helical shape.

(5) The method according to any one of (1) to (4), wherein two of the different patterns of two or more kinds are selected from a curved shape and a helical shape.

(6) The method according to (2) or (5), wherein the curved shape includes a plurality of circular arc shapes having different curvatures.

(7) The method according to (6), wherein at least one of the circular arc shapes having different curvatures exists on a plane that differs from a plane on which the other circular arc shapes exist.

(8) The method according to (5), wherein two of the different patterns of two or more kinds include a circular arc shape and a helical shape that are adjacent to each other, and a center axis of the helical shape is not in a perpendicular relationship with a plane on which the circular arc shape exists.

(9) The method according to any one of (1) to (8), wherein the secondary coil has one or more entire shapes selected from a generally linear shape, a generally wavy shape, a generally spiral shape, and a generally helical shape.

(10) The method according to any one of (1) to (9), wherein a shape in which two or more different patterns of two or more kinds are continuously arranged is given to the primary coil using a processing jig that is in contact with an outer side of the primary coil.

(11) The method according to any one of (1) to (9), wherein a shape in which two or more different patterns of two or more kinds are continuously arranged is given to the primary coil by inserting a shaping wire into the primary coil.

Advantageous Effects of Invention

According to the method for producing an in-vivo indwelling member according to the present invention, it is possible to easily produce an in-vivo indwelling member that can be more stably arranged inside a bump such as an aneurysm generated in a blood vessel such as an artery.

DESCRIPTION OF EMBODIMENT

Hereinbelow, an embodiment of a method for producing an in-vivo indwelling member according to the present invention will be described with reference to the drawings. The shape, the material, the size, the length, and the like of each member of a medical device described as an embodiment are shown as examples, and can be appropriately changed.

(1) Primary Coil Forming Step

In the present invention, a metal wire is first wound to form a primary coil in a primary coil forming step.

A method for winding the metal wire is not particularly limited. Examples of the method include a method for winding the metal wire around a core wire having a predetermined outer diameter and the like. By using such a core wire, a center axis L is easily formed as in primary coils 2, 3, and 4 illustrated in FIGS. 1(*a*) and 1(*b*), and 2. Further, when using the core wire, the core wire may be detached before a secondary coil forming step, or may also be detached after the secondary coil forming step (described below). When giving the primary coil a secondary coil shape using a shaping wire (described below), the core wire is preferably detached. The same wire may be used as both the shaping wire and the core wire, or different wires may also be used as the shaping wire and the core wire.

The material of the metal wire is not particularly limited. Examples of the material of the metal wire include platinum, tungsten, gold, tantalum, iridium, titanium, stainless, nickel, and an alloy containing two or more kinds of metals selected from these metals. The cross-sectional shape of the metal wire is not limited to a circular shape. Various shapes such as an elliptical shape and a square shape can be selected. When the cross-sectional shape of the metal wire is a circular shape, the diameter (wire diameter) thereof can be optionally selected within approximately $\phi$0.010 mm to 0.200 mm, although depending on the size of a bump. When the cross-sectional shape of the metal wire is not a circular shape, the maximum width thereof can be optionally selected within approximately 0.010 mm to 0.200 mm.

Figure 1:
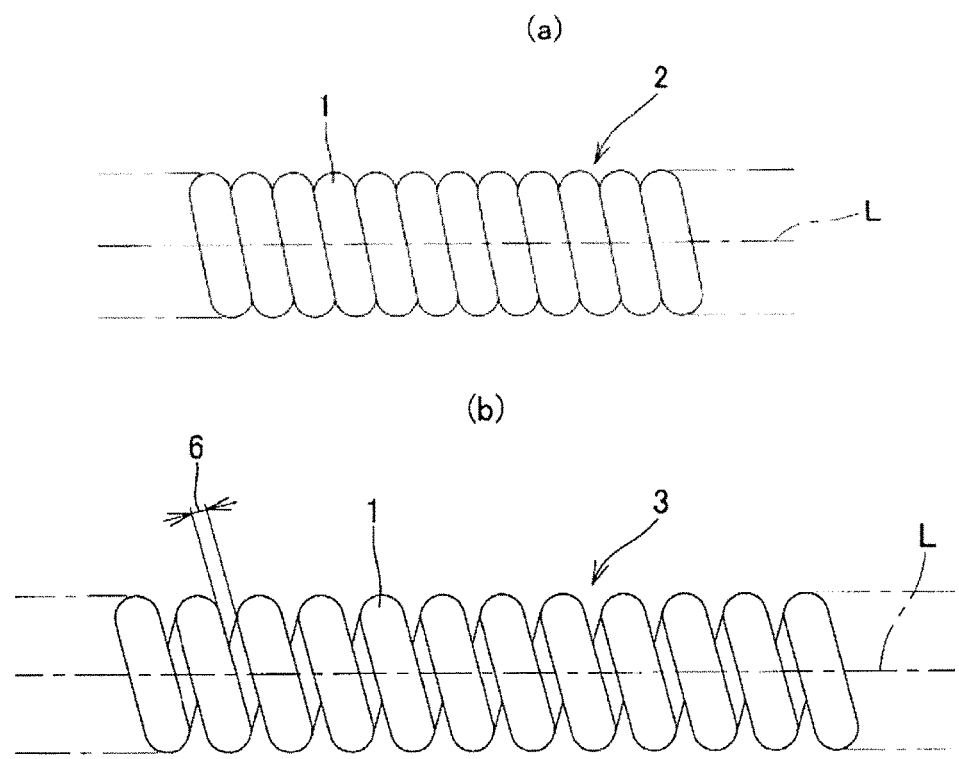
FIGS. 1(a) and 1(b) are schematic diagrams each illustrating an example of an embodiment of a primary coil used in the present invention.

A pitch interval of the primary coil is not particularly limited. For example, adjacent parts of the metal wire 1 may be in close contact with each other as illustrated in FIG. 1(*a*), or a predetermined interval 6 may be formed between adjacent parts of the metal wire as illustrated in FIG. 1(*b*).

Figure 2:
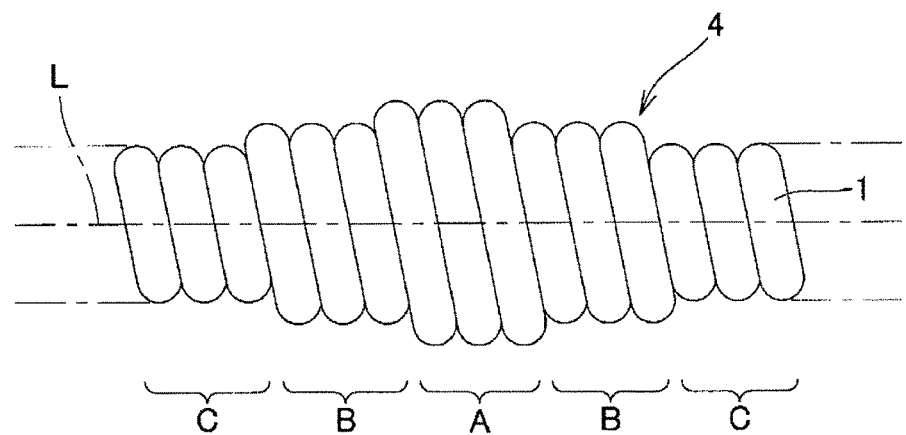
FIG. 2 is a schematic diagram illustrating another example of the embodiment of the primary coil used in the present invention.
Figure 3:
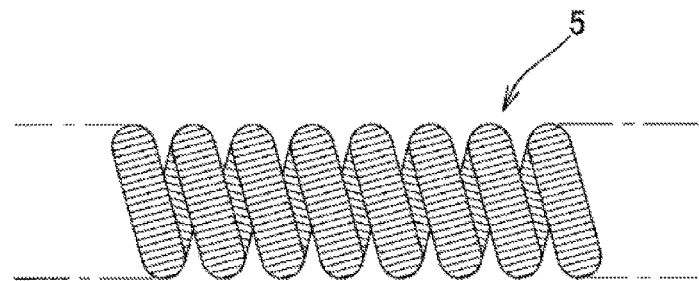
FIG. 3 is a schematic diagram of the form of a general secondary coil.

The outer diameter of the primary coil formed by winding such a metal wire may be appropriately selected in accordance with the size of an inner cavity of a microcatheter or the like which is used for guiding an in-vivo indwelling member to be finally obtained to the bump. For example, when a microcatheter for 0.010 inch (0.254 mm) to 0.018 inch (0.457 mm) is used, the outer diameter may be set to ϕ0.20 mm to ϕ0.45 mm. Further, the outer diameter of the primary coil may be uniform throughout the entire length thereof, or may also be optionally varied. For example, when a microcatheter for 0.010 inch to 0.018 inch is used, the outer diameter may be partially varied within ϕ0.2 mm to ϕ0.45 mm as in the primary coil 4 illustrated in FIG. 2. In the example illustrated in FIG. 2, the primary coil has a shape in which a part A having the largest outer diameter when winding the metal wire 1, a part B having a smaller outer diameter than the part A, and a part C having a smaller outer diameter than the part B are sequentially continuously arranged such as C, B, A, B, C, and so on. However, the order of the parts A, B, and C is not limited thereto. Further, the size of the outer diameter is not limited to the three kinds as illustrated in FIG. 2, and may be two or four or more kinds. The primary coil as illustrated in FIG. 2 can be manufactured, for example, using a core wire that has a step or a tapered shape.

(2) Secondary Coil Forming Step

<1> Shape of Secondary Coil

In the secondary coil forming step, a shape in which two or more different patterns of two or more kinds are continuously arranged is given to the primary coil obtained in the above step of (1).

The "pattern" is not particularly limited. Examples of the pattern include a linear shape, a wavy shape, a curved shape, a bent shape, a helical shape, a combination of two or more kinds of these shapes, and any other shapes.

The wavy shape is only required to have an undulating line shape. Examples of the wavy shape include a continuous line shape in which the amplitude and the wavelength each vary in a fixed or any manner and the like.

The curved shape is not particularly limited as long as it has a continuously curved line shape with no corner. However, the curved shape is defined to include one other than the wavy shape and the helical shape. Examples of such a curved shape include a circular arc shape, an elliptical arc shape, and the like. Further, circular arc patterns of circular arc shapes having different curvatures are regarded as different patterns, and patterns of elliptical arc shapes having different long diameters and/or short diameters are regarded as different patterns.

The bent shape is not particularly limited as long as it has a bent line shape. However, the bent shape is defined to include one other than the wavy shape and the curved shape.

Examples of the helical shape include a shape such as a spiral in which circular arcs are formed on substantially the same plane and a shape having a three-dimensional structure such as a cylindrical shape and a polygonal cylindrical shape each having a structure in which the outer diameter is constant in the length direction, a cylindrical shape and a polygonal cylindrical shape each having a structure in which the outer diameter varies (differs) in the length direction, a generally conical shape, and a generally polygonal pyramid shape. Further, the helical shape includes one having less than a single turn, for example, a half turn and an approximately half turn in addition to one having a single turn and one having a plurality of turns.

Further, two or more kinds of these shapes may be combined in a single pattern.

A combination of different patterns is not particularly limited, and may be appropriately selected from the above patterns by taking into consideration the shape and the like of a bump such as an aneurysm inside which an in-vivo indwelling member to be finally obtained is arranged. For example, when a helical shape having a constant outer diameter is included as one of the different patterns, an in-vivo indwelling member is likely to be in close contact with a bump having a generally perfect spherical shape and stably arranged therein. On the other hand, when a helical shape having a varying outer diameter is included as one of the different patterns, an in-vivo indwelling member is likely to be in close contact with not a bump having a generally perfect spherical shape, but a bump having a distorted shape and stably arranged therein. Further, the helical shape and at least one shape selected from the linear shape, the wavy shape, the curved shape, and the bent shape may be combined, and two or more shapes selected from the linear shape and the helical shape may also be combined. In terms of arranging an in-vivo indwelling member along an inner wall of a bump in a blood vessel, it is preferred to select a round shape which is easily arranged along a curved surface of the inner wall of the bump. For example, it is more preferred to select a combination of two or more shapes selected from the curved shape and the helical shape.

Examples of a pattern in which two or more curved shapes are combined include a pattern that includes a plurality of circular arc shapes having different curvatures. In particular, at least one of these circular arc shapes is preferably arranged so as to exist on a plane that differs from a plane on which the other circular arc shapes exist. Further, the "plane" on which a circular arc shape exists indicates a plane on which a center axis line of the primary coil which forms the circular arc shape exists. Further, it is not strictly required that the center axis lines of the circular arc shapes exist on the same plane.

Examples of a pattern in which the curved shape and the helical shape are combined include a pattern in which a curved shape (a circular arc shape, for example), and a helical shape (a helical shape having a half turn, for example) are arranged adjacent to each other so that the center axis of the helical shape is not in a perpendicular relationship with a plane on which the curved shape exists and a pattern in which the center axis is in a perpendicular relationship with the plane. However, the pattern is not limited thereto.

The size of the pattern (length, width) is not particularly limited. However, as will described below, when the shape of an inner hollow section of a shaping mold is a generally spherical shape and a helical shape is used as a pattern, it is preferred to set the width (outer diameter) of the helical shape so that the maximum width of the generally spherical inner hollow section is equal to or less than the minimum outer diameter of the helical pattern. Accordingly, a part having the helical shape in the secondary coil inserted into the shaping mold is easily arranged along substantially the entire inner wall surface that forms the inner hollow section, which makes it easy to form a generally spherical three-dimensional structure closer to a hollow shape.

Among the above shapes, the "different patterns", of course, include different shapes. Further, also when a plurality of shapes that are the same as each other are continuously arranged and adjacent ones of the shapes are arranged at a predetermined angle, the shapes are regarded as the different patterns. For example, in a case where there are two wavy patterns which extend in the same direction as the axial direction of the secondary coil and are formed on the same plane, when the two planes form a predetermined angle in a direction perpendicular to the axial direction of the secondary coil on the plane on which the wavy patterns exist, when the center axes of the wavy shapes form a predetermined angle, and when a combination of the above cases, even when the two patterns have the same shape, the patterns are regarded as different patterns.

"Two or more patterns are continuously arranged" indicates that, among the above patterns, two or more different patterns exist and the patterns are arranged so that adjacent patterns differ from each other. Further, the way of continuously arranging different patterns is not particularly limited as long as adjacent patterns differ from each other in the secondary coil to be formed. When adjacent patterns differ from each other, the rigidity varies in the boundary between the patterns. Accordingly, in insertion of the secondary coil into a shaping mold having an inner hollow section, when the secondary coil which is sequentially inserted makes contact with a wall surface that forms the inner hollow section, it becomes possible to allow the secondary coil to travel in any direction. Therefore, it becomes easy to arrange a part of the secondary coil, the part being inserted into the inner hollow section, so as to extend along the entire inner wall surface that forms the inner hollow section. As a result, the secondary coil is shaped to have a three-dimensional structure that corresponds to the inner wall surface as the appearance shape thereof. Further, "being adjacent" indicates a case where patterns are directly adjacent to each other. However, "being adjacent" is a concept that includes a case where there is a slight deformation in a switching part between patterns.

The entire shape of the secondary coil used in the present invention is not particularly limited as long as the effect of the present invention can be obtained. The secondary coil is only required to have one or more entire shapes selected from a generally linear shape, a generally wavy shape, a generally spiral shape, and a generally helical shape.

An embodiment of the secondary coil used in the present invention will be described with reference to FIGS. 4(a) to 4(e), 5(a) and 5(b), 7(a) to 9(b).

Figure 4:
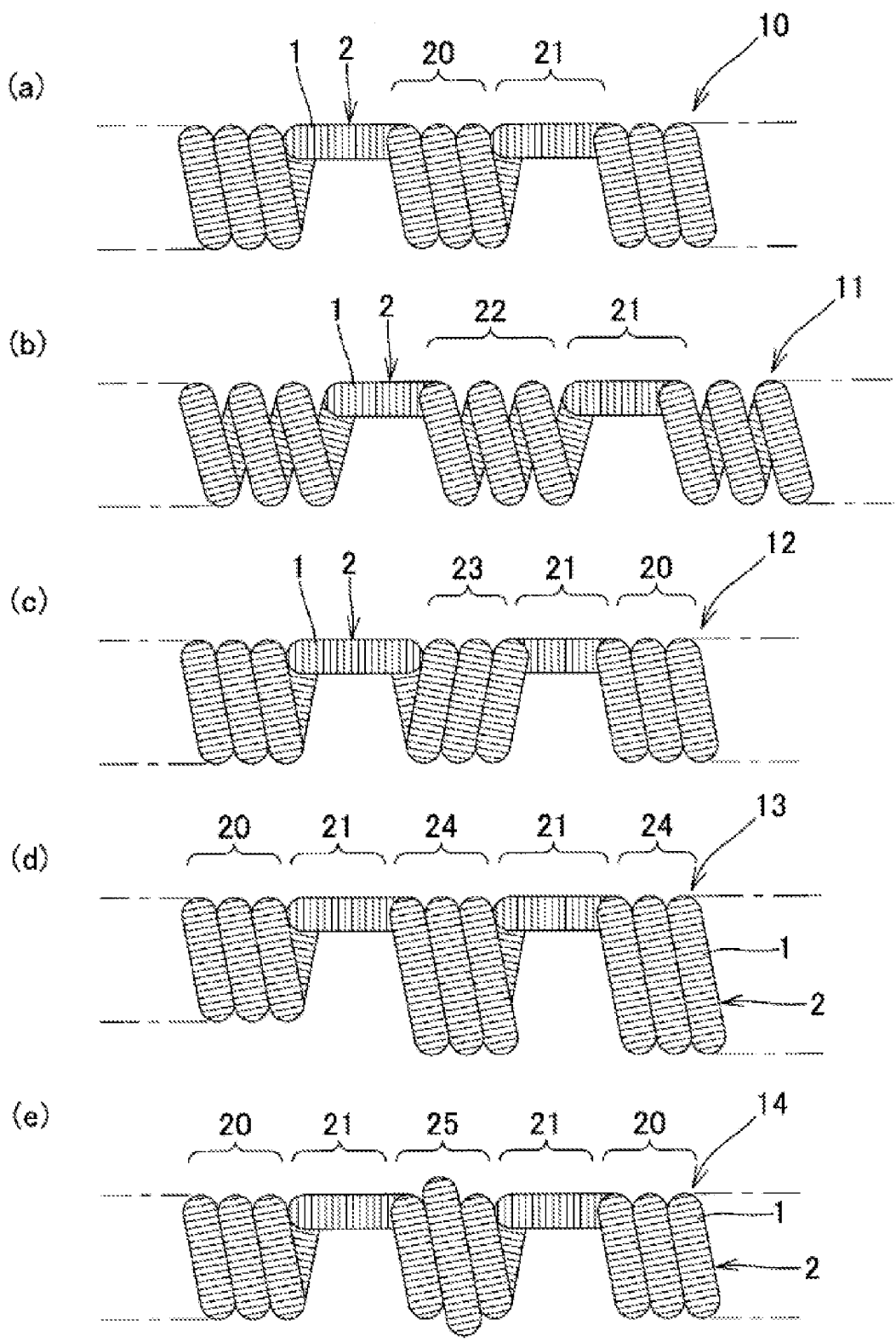
FIGS. 4(a) to 4(e) are schematic diagrams each illustrating an example of an embodiment of a secondary coil used in the present invention.

A secondary coil 10 illustrated in FIG. 4(a) is formed using the primary coil 2 which is formed of the metal wire 1 illustrated in FIG. 1(a) (first example). The secondary coil 10 is a linear secondary coil in which two different patterns, specifically, a helical pattern 20 and a linear pattern 21 are mutually continuously arranged. In the first example, the helical pattern 20 is tightly wound so that adjacent parts of the primary coil 2 have no winding interval therebetween and have the same travelling direction (winding direction) and the same outer diameter of the helix. In the first example, linear patterns 21 are arranged on the same position throughout the entire length of the secondary coil 10. However, the linear patterns 21 may be arranged at different positions in the axial direction of the secondary coil. Further, the number of turns of the helix may be optionally changed.

A secondary coil 11 illustrated in FIG. 4(b) (second example) is the same as the first example illustrated in FIG. 4(a) excepting that a helical pattern is wound with a pitch so that adjacent parts of the primary coil 2 have a predetermined interval therebetween. A pitch interval (or an interval between adjacent parts of the primary coil) is not particularly limited, and can be appropriately selected.

In a secondary coil 12 illustrated in FIG. 4(c) (third example), the structure of each pattern is the same as the first example illustrated in FIG. 4(a) excepting the following point. In the third example, the same helical pattern 20 as illustrated in FIG. 4(a) and a helical pattern 23 that differs from the pattern 20 only in the travelling direction (winding direction) of the helix are used as helical patterns. Therefore, the secondary coil 12 has a shape in which three different patterns are continuously arranged. In the third example, the pattern 20 and the pattern 23 are mutually repeatedly arranged with the linear pattern 21 interposed therebetween. However, the arrangement of these patterns is not limited thereto. It is only required that the patterns 20 and 23 be arranged in any manner and connected to each other through the linear pattern 21 in the length direction of the secondary coil.

In a secondary coil 13 illustrated in FIG. 4(d) (fourth example), the structure of each pattern is the same as the first example illustrated in FIG. 4(a) excepting the following point. In the fourth example, the same helical pattern 20 as illustrated in FIG. 4(a) and a helical pattern 24 that differs from the pattern 20 in the outer diameter of the helix are used as helical patterns. Therefore, the secondary coil 13 has a shape in which three different patterns are continuously arranged. In the fourth example, the helical patterns 20 and 24 are randomly arranged with the linear pattern 21 interposed therebetween. However, the patterns 20 and 24 may be alternately arranged with the linear pattern 21 interposed therebetween.

In a secondary coil 14 illustrated in FIG. 4(e) (fifth example), the structure of each pattern is the same as the first example illustrated in FIG. 4(a) excepting the following point. In the fifth example, the same helical pattern 20 as illustrated in FIG. 4(a) and a helical pattern 25 that differs from the pattern 20 in the outer diameter of the helix are used as helical patterns. Therefore, the secondary coil 14 has a shape in which three different patterns are continuously arranged. In the helical pattern 25, the outer diameter of the helix is varied in the axial direction. In the fifth example, the helical pattern 25 has a structure that has the maximum outer diameter in a generally central part and a smaller outer diameter on both sides thereof. However, a way of varying the outer diameter is not limited thereto, and the outer diameter may be varied in any manner. In the fifth example, the patterns 20 and 25 are mutually repeatedly arranged with the linear pattern 21 interposed therebetween. However, the arrangement of these patterns is not limited thereto. It is only required that the patterns 20 and 25 be arranged in any manner and connected to each other through the linear pattern 21 in the length direction of the secondary coil.

In the first to fifth examples of the embodiment illustrated in FIGS. 4(a) to 4(e), the helical patterns and the linear patterns are arranged in a generally linear form so that the secondary coil is generally linear in its entire shape. That is, in the first to third and fifth examples, the center axes of the helixes of the helical patterns 20, 22, 23, and 25 are all located on the same straight line. The straight line and the linear patterns 21 are in a parallel relationship throughout the entire length of the secondary coil. Further, also in the fourth example, the center axes of the helixes of the helical patterns 24 are close to and in a parallel relationship with the center axes of the helixes of the helical patterns 20 on the same plane as a plane formed by the center axes of the helixes of the helical patterns 20 and the linear patterns 21.

In the present invention, in addition to the above relationships in which the center axes of the helical patterns are arranged on the same straight line in the length direction of the secondary coil, the angle of a direction perpendicular to the center axis in the length direction of the secondary coil may be optionally changed.

Figure 5:
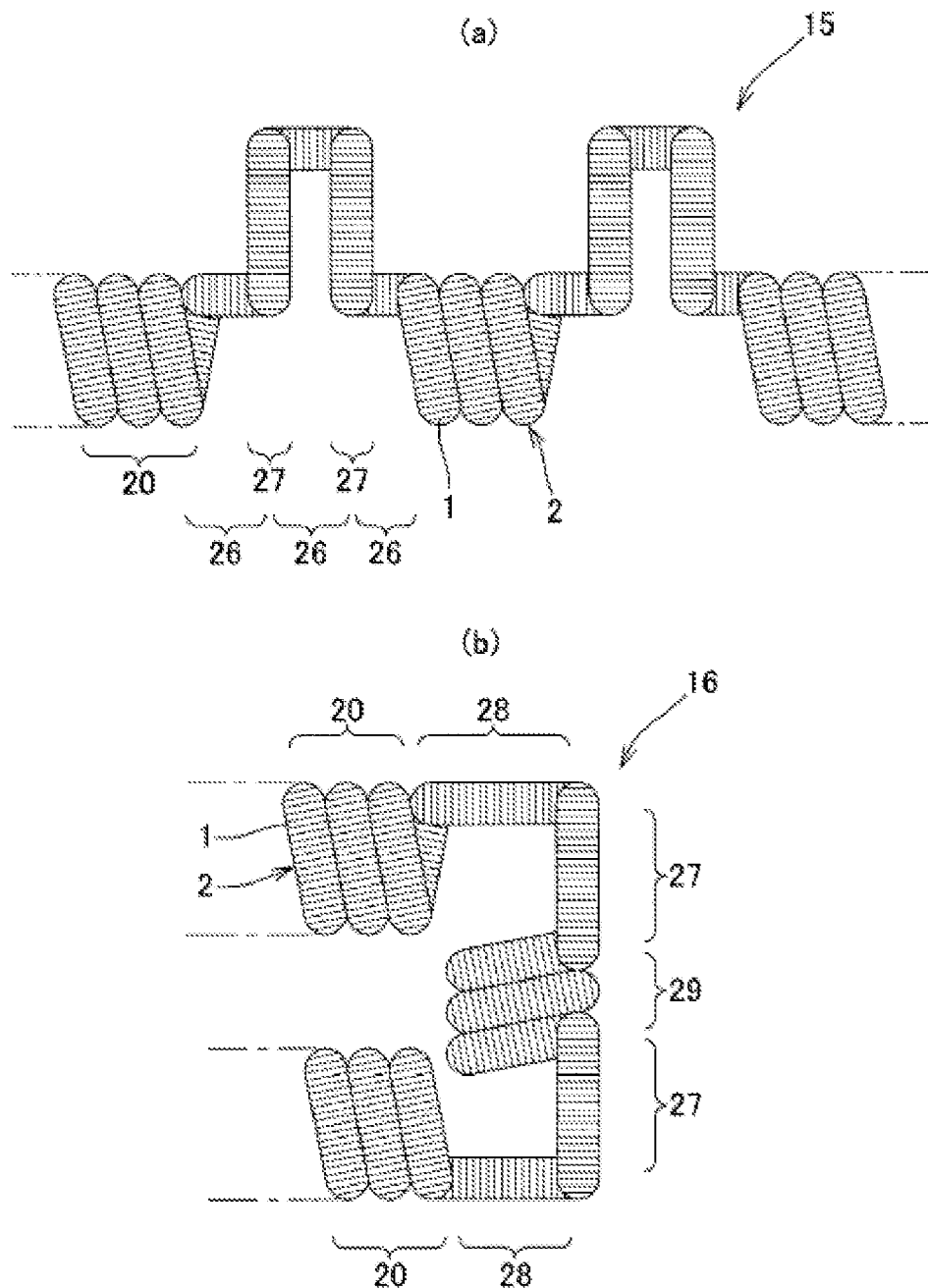
FIGS. 5(a) and 5(b) are schematic diagrams each illustrating another example of the embodiment of the secondary coil used in the present invention.

A secondary coil 15 illustrated in FIG. 5(a) (sixth example) is formed using the primary coil 2 which is formed of the metal wire 1. In the secondary coil 15, three different patterns, specifically, the helical pattern 20, a curved (circular arc or elliptical circular arc) pattern 27, and a linear pattern 26 are continuously arranged. In the sixth example, the center axis in the length direction of the linear pattern 26 is defined as the center axis in the length direction of the secondary coil 15. The center axis in the length direction of the helical pattern 20 and the center axis of the circular arc pattern 27 are opposed to each other with respect to the center axis of the secondary coil. The entire shape of the secondary coil 15 of the sixth example is a generally wavy shape.

A secondary coil 16 illustrated in FIG. 5(b) (seventh example) is formed using the primary coil 2 which is formed of the metal wire 1. In the secondary coil 16, four different patterns, specifically, helical patterns 20 and 29, a curved (semicircular arc) pattern 27, and a linear pattern 28 are continuously arranged. In the seventh example, the center axes in the length direction of two helical patterns 20 and the center axis in the length direction of a single helical pattern 29 form a U shape. By continuously arranging U-shape parts, the entire shape of the secondary coil 16 can be formed into a generally wavy shape and a generally helical shape.

The entire shape of the secondary coil is not limited to the shapes illustrated in FIGS. 5(a) and 5(b), and various patterns can be combined to form various shapes.

A secondary coil 17 illustrated in FIGS. 7(a) to 7(c) (eighth example) is formed using the primary coil 2 which is formed of the metal wire 1 illustrated in FIG. 1(a). FIG. 7(a) is a perspective view schematically illustrating an outline of the secondary coil 17. FIG. 7(b) is a line diagram simplifying a side view of the secondary coil 17. FIG. 7(c) is a line diagram simplifying a plan view of the secondary coil 17. In the secondary coil 17, two circular arc patterns having different curvatures exist on a plurality of different planes and these different four patterns are continuously arranged regularly and sequentially to form one combination. Further, a plurality of combinations are continuously arranged so that the secondary coil 17 has a linear shape along a center axis M as a whole.

In the eighth example, circular arcs that form circular arc patterns denoted by reference signs 50 and 52 in FIGS. 7(a) to 7(c) have the same curvature, circular arcs that form circular arc patterns denoted by reference signs 51 and 53 also have the same curvature, and the circular arcs that form the patterns 50 and 52 have a different curvature from the curvature of the circular arcs that form the patterns 51 and 53. The circular arcs that form the patterns 50 and 52 have a smaller radius and a larger curvature than the circular arcs that form the patterns 51 and 53. In this example, the circular arc patterns 50, 51, 52, and 53 are all generally semicircular arcs. The curvature of each of the circular arcs can be appropriately changed.

Further, the circular arcs that form the circular arc patterns 50, 51, 52, and 53 respectively exist on different planes W, X, Y, and Z. When angles formed between the plane W and the plane X, between the plane X and the plane Y, between the plane Y and the plane Z, and between the plane Z and the plane W are respectively denoted by angles α, β, γ, and δ, because the plane W and the plane Y are parallel to each other, the angle α and the angle β are equal to each other, the angle γ and the angle δ are equal to each other, and the angle β and the angle γ are also made equal to each other in the example illustrated in FIGS. 7(a) to 7(c). In the eighth example, the center axis L (see FIGS. 1(a) and 1(b)) of the primary coil 2 exists on each of the planes. The angles α, β, γ, and δ can be appropriately independently changed.

A secondary coil 18 illustrated in FIGS. 8(a) to 8(c) (ninth example) is formed using the primary coil 2 which is formed of the metal wire 1 illustrated in FIG. 1(a). FIG. 8(a) is a perspective view schematically illustrating an outline of the secondary coil 18. FIG. 8(b) is a line diagram simplifying a side view of the secondary coil 18. FIG. 8(c) is a line diagram simplifying a plan view of the secondary coil 18.

In the secondary coil 18, two of the different patterns of two or more kinds include circular arc patterns 60 and 62 and helical patterns 61 and 63, the circular arc patterns 60 and 62 and the helical patterns 61 and 63 being adjacent to each other. A center axis N of the helical patterns 61 and 63 is not in a perpendicular relationship with planes W' and Y' on which the circular arc patterns 60 and 62 exist. In the ninth example, axes O and P which are perpendicular to the planes W' and Y' are perpendicular to the center axis N, and the planes W' and Y' are in a parallel relationship with the center axis N. Further, the axis O and the axis P are parallel to each other.

In the ninth example, the circular arc pattern 60 and the circular arc pattern 62 have the same curvature. The outer diameter of the circular arc patterns 60 and 62 is smaller than the helical diameter (outer diameter) of the helical patterns 61 and 63. The helical pattern 61 and the helical pattern 63 have different winding directions, but have the same number of turns, specifically, one and a half turns and also have the same pitch. The curvature of the circular arc patterns 60 and 62 and the number of turns and the pitch of the helical patterns 61 and 63 can be appropriately changed.

A secondary coil 19 illustrated in FIGS. 9(a) and 9(b) (tenth example) is a modification of the secondary coil 18 illustrated in FIGS. 8(a) to 8(c). A perspective appearance is similar to the eighth example (FIG. 7(a)). The coil 19 of the tenth example is the same as the ninth example excepting that the number of turns of the helical shape 61 and the helical shape 63 is changed to a half turn and the pitch thereof is made larger in the secondary coil 18. FIG. 9(a) is a line diagram simplifying a side view of the secondary coil 19. FIG. 9(b) is a line diagram simplifying a plan view of the secondary coil 19. In FIGS. 9(a) and 9(b), helical shapes of the tenth example are denoted by reference signs 64 and 65, and the same structure as the structure of the secondary coil 18 illustrated in FIGS. 8(a) to 8(c) is denoted by the same reference sign.

<2> Method for Manufacturing Secondary Coil

Although a method for manufacturing the secondary coil used in the present invention is not particularly limited, examples of the method in the case of the secondary coils as illustrated in FIGS. 4(a) to 4(c) and FIGS. 7(a) to 9(b) will be described respectively with reference to FIGS. 6(a) to 6(c) and FIG. 10. Hereinbelow, (i) a method using a processing jig that is in contact with the outer side of the primary coil and (ii) a method of inserting a shaping wire into the primary coil will be described.

(i) Method Using Processing Jig in Contact with Outer Side of Primary Coil

Methods illustrated in FIGS. 6(a) to 6(c) respectively use processing jigs 30, 31, and 32 which are in contact with the outer side of the primary coil. Specifically, the primary coil is wound around the processing jig 30, 31 or 32 so that the outer side of the primary coil is in contact with the outer side of the processing jig 30, 31, or 32 to thereby directly give the primary coil a desired shape.

The processing jig 30 illustrated in FIG. 6(a) includes a mandrel 33 having a desired outer diameter and at least a pair of projections 36 provided on the surface of the mandrel 33. A linear pattern in the secondary coil is formed between the projections 36 of the processing jig 30 and helical patterns are formed on both sides thereof. By providing the projections 36, it is possible to easily form the linear pattern between the helical patterns. In the example illustrated in the drawing, the primary coil 2 is hooked on the same side of the projections 36 so that travelling directions (rotation directions) of helixes in the helical patterns are made different from each other. However, when the primary coil 2 is hooked on the opposite side in one of the projections 36, it is possible to change the travelling direction of the helix.

Figure 6:
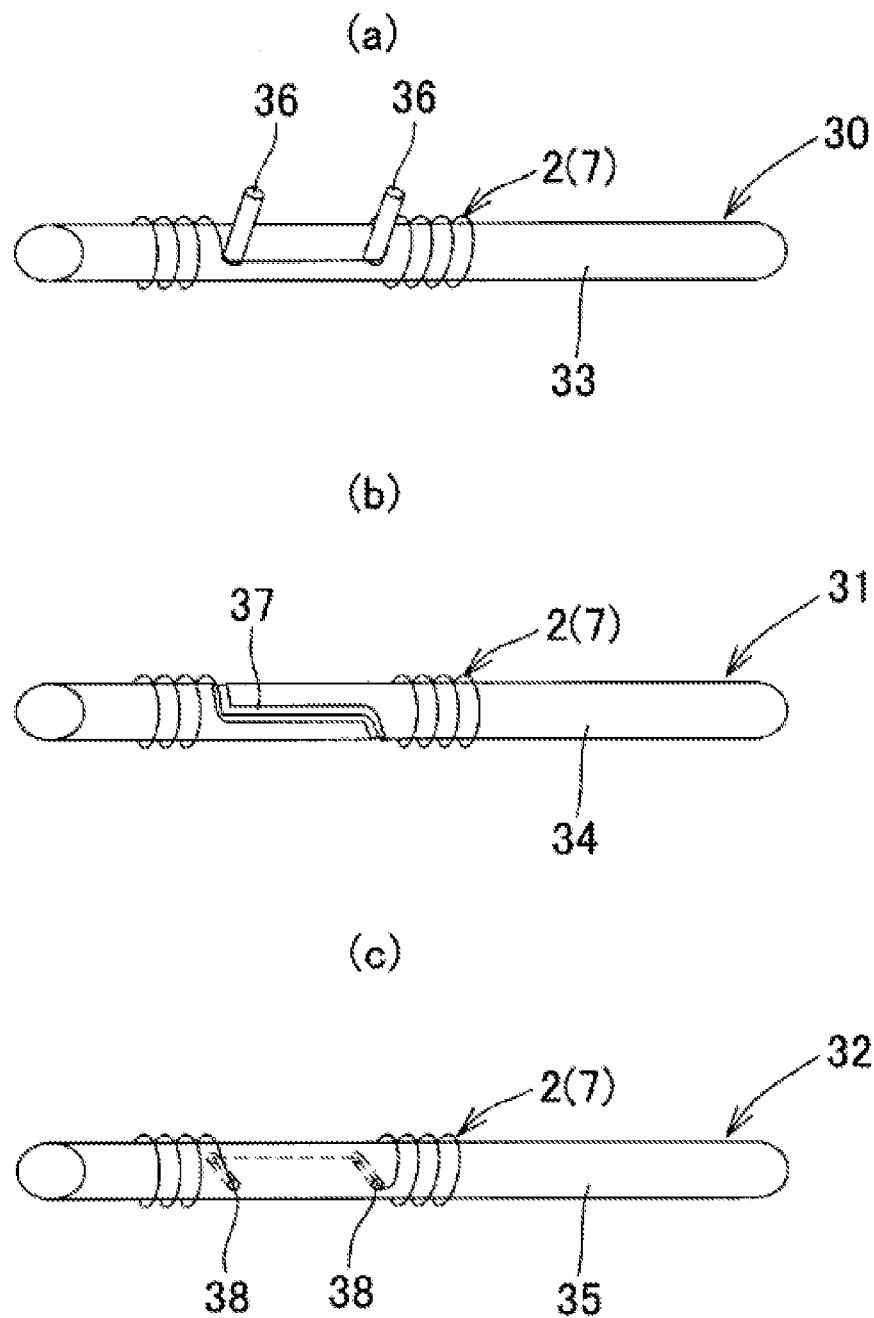
FIGS. 6(a) to 6(c) are schematic diagrams each illustrating an example of an embodiment of a method for producing the secondary coil used in the present invention.

The processing jig 31 illustrated in FIG. 6(*b*) includes a mandrel 34 having a desired outer diameter and, on the surface of the mandrel 34, at least one groove 37 is provided which has a shape corresponding to the linear pattern and a part of each of the helical patterns continuous with both ends of the linear pattern in the secondary coil. The groove makes it possible to easily form the linear pattern between the helical patterns. In the example illustrated in the drawing, the direction of the groove corresponding to a part of the helical pattern differs in both ends of the linear pattern. However, the direction may be the same in both ends. Accordingly, the travelling directions of the helixes of the helical patterns on both ends of the linear pattern can be optionally set.

The processing jig 32 illustrated in FIG. 6(*c*) includes a mandrel 35 having a desired outer diameter and at least a pair of through holes 38 formed on the mandrel 35 with a predetermined interval therebetween. The primary coil 2 is inserted through the through holes 38, a linear pattern of the secondary coil is formed between the through holes 38, and helical patterns can be formed on both sides thereof.

Figure 10:
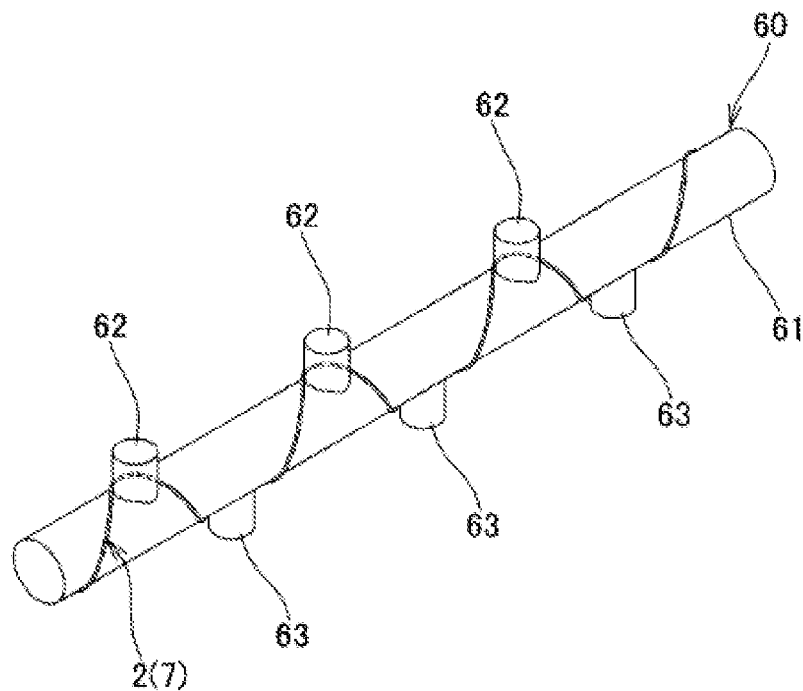
FIG. 10 is a schematic diagram illustrating another example of the method for manufacturing the secondary coil used in the present invention.

A method illustrated in FIG. 10 also uses a processing jig 60 which is in contact with the outer side of the primary coil. The processing jig 60 illustrated in FIG. 10 includes a mandrel 61 having a desired outer diameter and a plurality of cylindrical projections 62 and 63 provided on the outer peripheral surface of the mandrel 61. In the example illustrated in FIG. 10, a plurality of projections 62 are arranged at intervals in a row on the surface of the mandrel 60 in parallel to the center axis direction of the mandrel 60. In addition, a plurality of projections 63 are arranged at intervals in a row on the surface of the mandrel 60 in parallel to the center axis direction of the mandrel 60 on a side opposite to the side on which a row of the projections 62 is arranged. The projections 62 and 63 are arranged so that no projection 63 exists on the exact opposite position of each of the projections 62 and no projection 62 exists on the exact opposite position of each of the projections 63. In this example, for example, each of the projections 63 is arranged on the opposite side of an intermediate position between adjacent projections 62. Further, each of the projections 62 is arranged on the opposite side of an intermediate position between adjacent projections 63.

Although not illustrated in FIG. 10, for example, a guide groove may be provided on the outer peripheral surface of the mandrel 60 and/or the outer peripheral surfaces of the projections 62 and 63 so that circular arcs formed by the primary coil 2 which is wound in contact with the outer peripheral surfaces of the mandrel 60, and the projections 62 and 63 can easily exist on the same plane.

Figure 7:
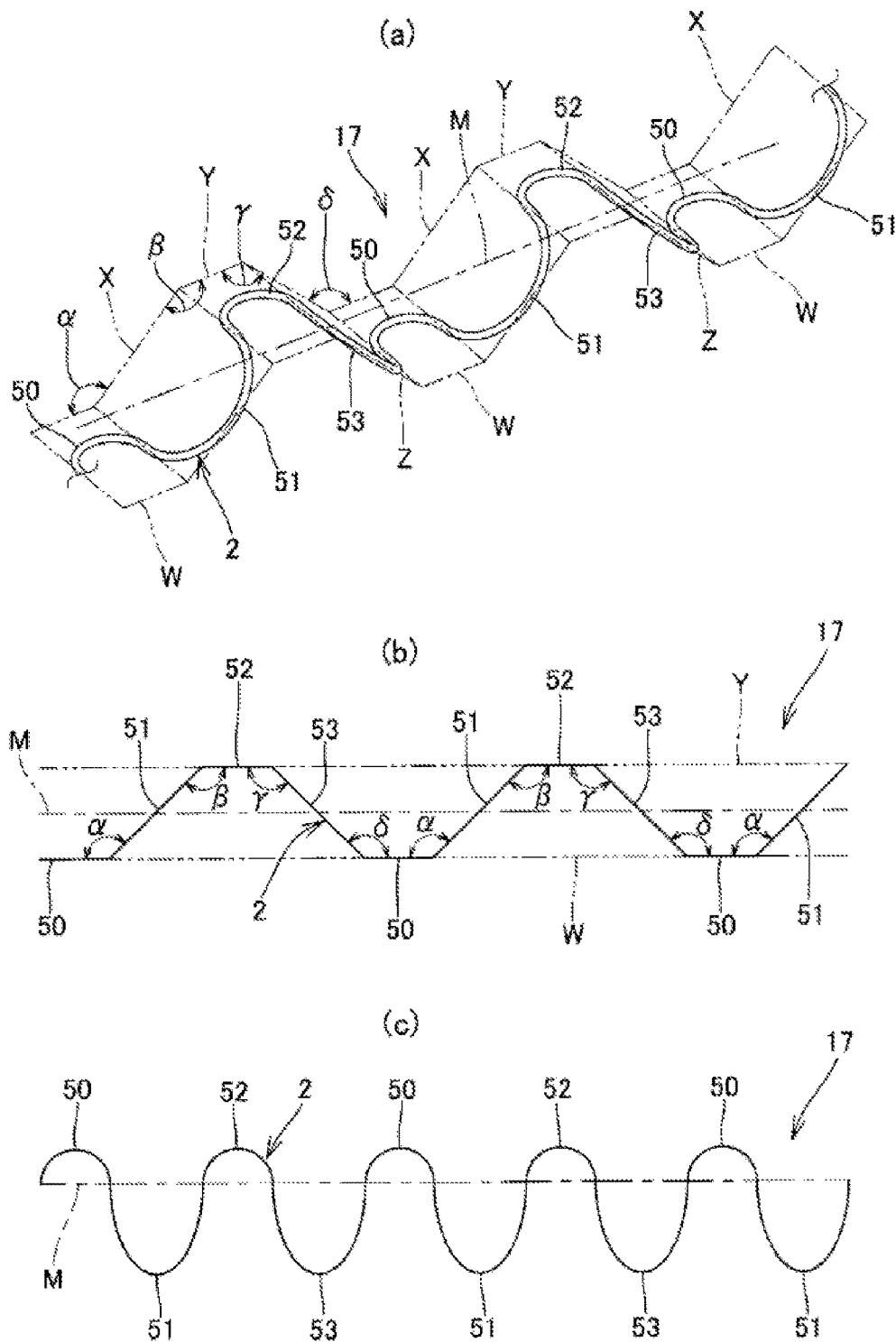
FIGS. 7(a) to 7(c) are schematic diagrams each illustrating still another example of the embodiment of the secondary coil used in the present invention.
Figure 9:
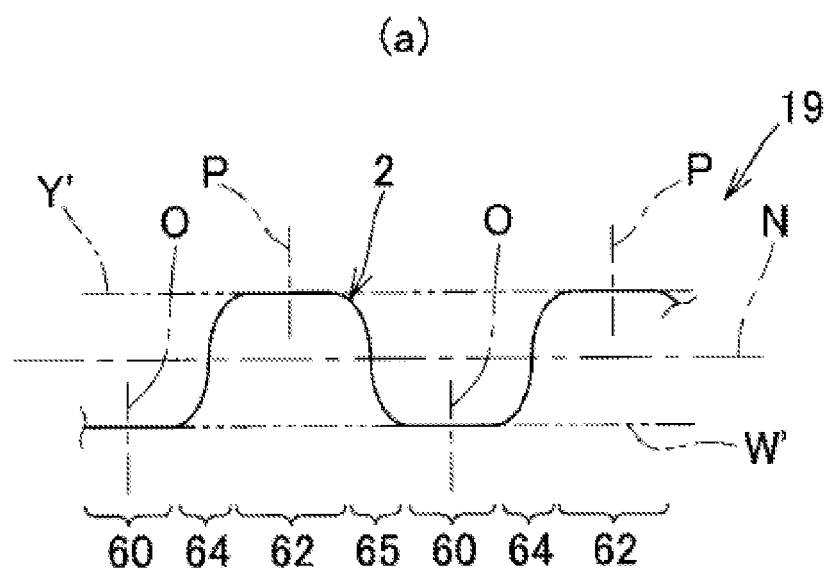
FIGS. 9(a) and 9(b) are schematic diagrams each illustrating still another example of the embodiment of the secondary coil used in the present invention.
Figure 9:
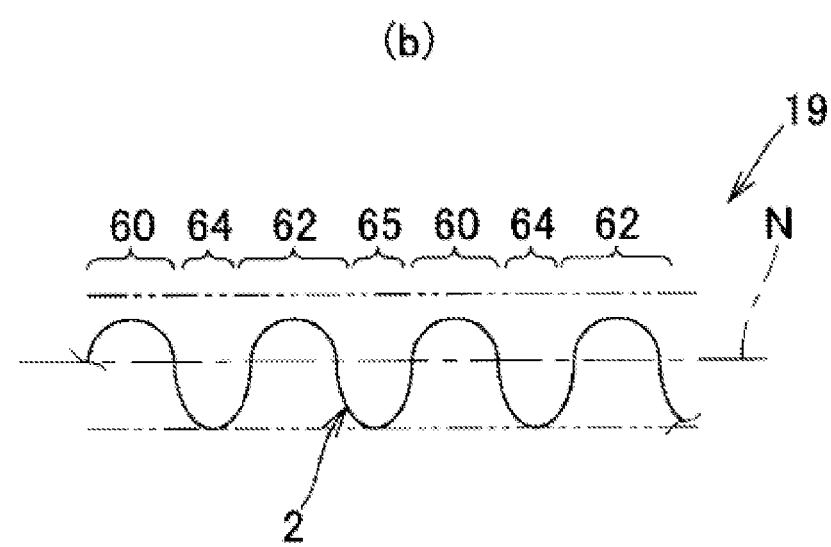

As illustrated in FIG. 10, the secondary coil having the shape illustrated in FIGS. 7(*a*) to 7(*c*) or FIGS. 9(*a*) and 9(*b*) can be formed by winding the primary coil 2 on the mandrel 61 and the projections 62 and 63 of the processing jig 60 by approximately halfway around for each turn and fixing the primary coil thereto.

Figure 8:
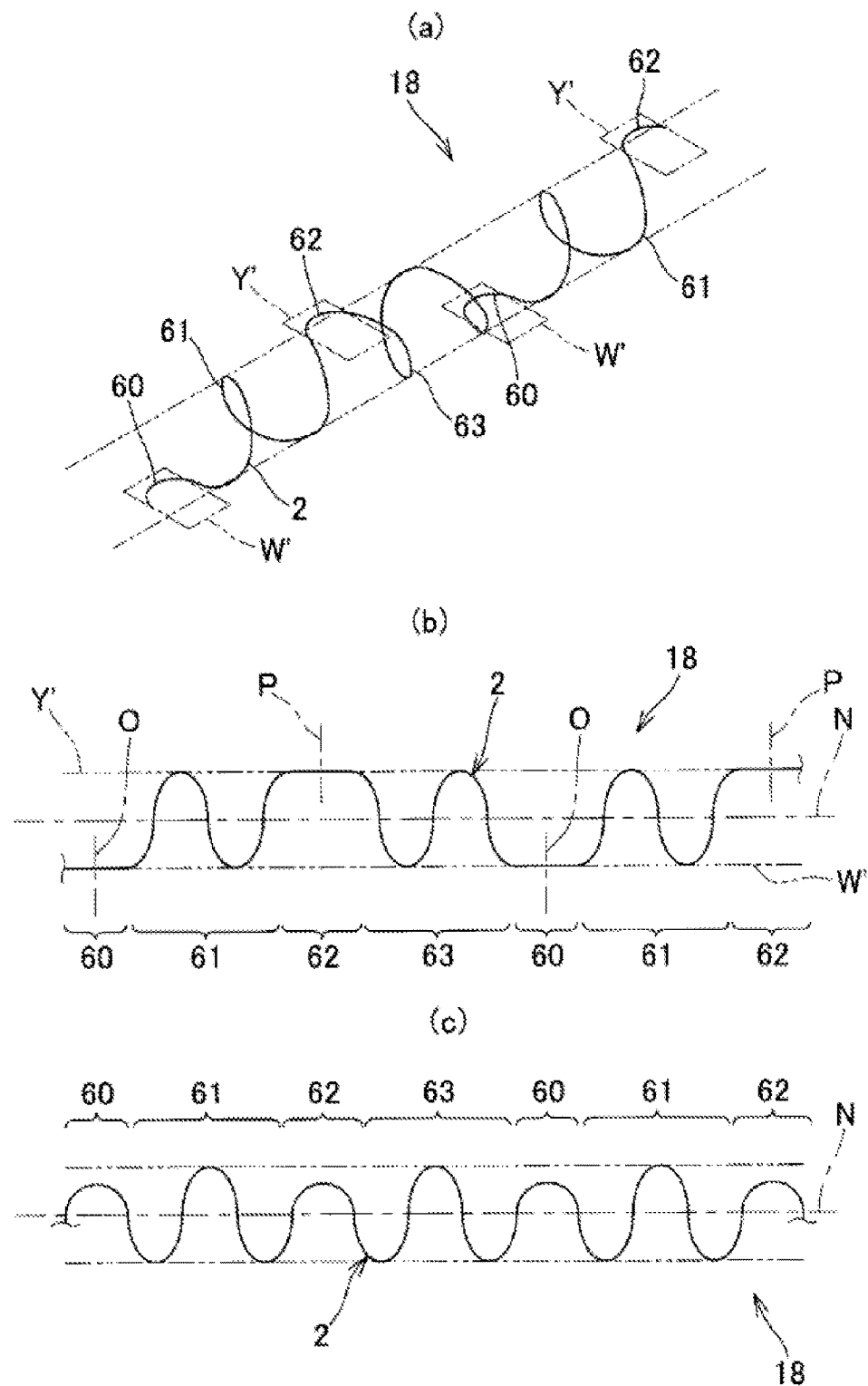
FIGS. 8(a) to 8(c) are schematic diagrams each illustrating still another example of the embodiment of the secondary coil used in the present invention.

In the processing jig 60 illustrated in FIG. 10, for example, the secondary coil having the shape illustrated in FIG. 8 and a secondary coil having a shape in which a plurality of helical shapes having different outer diameters and different center axis directions are continuously arranged can be formed by appropriately changing the number of turns of the primary coil 2 on the mandrel 61 and the projections 62 and 63, a distance between the projections 62, and the arrangement of the projections 62.

(ii) Method for Inserting Shaping Wire into Primary Coil

In this method, a shaping wire that previously has a desired secondary coil shape is inserted into the primary coil and the shape of the shaping wire is transferred to the primary coil to thereby give the primary coil a shape in which two or more different patterns of two or more kinds are continuously arranged.

Therefore, in this method, the shaping wire having a desired shape is first manufactured. When manufacturing the shaping wire, for example, the processing jig used in (i) can be used. Description will be made with reference to FIGS. 6(*a*) to 6(*c*) and 9(*a*) and 9(*b*). A wire 7 is wound around the processing jig 30, 31, 32, or 60 instead of the primary coil 2 in FIGS. 6(*a*) to 6(*c*) and 9(*a*) and 9(*b*) to thereby give the wire 7 a desired shape. As necessary, heat treatment is performed in the same manner as in the case of the primary coil as will be described below. Then, the wire 7 is detached from the processing jig to obtain the shaping wire 7. Thereafter, the shaping wire 7 is inserted into the primary coil to thereby give the primary coil a desired secondary coil shape.

(iii) Common Matters in (i) and (ii)

The material of each of the processing jigs illustrated in FIGS. 6(*a*) to 6(*c*) and 10 and the material of the wire used as the shaping wire are not particularly limited. Examples of the materials include metal such as stainless, a shape memory alloy, and the like. As the wire used as the shaping wire, a shape memory alloy is preferably used in terms of detachment from the processing jig and insertion into the primary coil.

In the present invention, after the primary coil is directly wound in contact with the outer peripheral surface of the processing jig as described in (i) or after the shaping wire is inserted into the primary coil as described in (ii), heat treatment may be performed thereon. Accordingly, the shape in a state arranged in the processing jig can be further fixed. Although the heating temperature is not particularly limited, the heating temperature is preferably 300° C. to 600° C. in terms of more effectively fixing the shape. Further, the atmosphere of the heat treatment is also not particularly limited. Examples of the atmosphere include air, vacuum, inert gas such as nitrogen and argon, and reducing gas such as hydrogen and hydrogen mixed gas.

Further, when the secondary coil includes a helical shape and an inner hollow section of a shaping mold used in the next step is generally spherical, it is preferred to previously adjust the outer diameter of the helical pattern part so that, as the minimum outer diameter of the helical pattern part of the secondary coil after the heat treatment, the maximum width of the generally spherical inner hollow section is equal to or less than the minimum outer diameter of the helical shape. When the outer diameter of the helical shape is substantially constant, it is more preferred to previously adjust the outer diameter of the helical pattern part so that the maximum width of the generally spherical inner hollow section is equal to or slightly smaller than the outer diameter of the helical shape.

The processing jig and the shaping wire are detached after heat treatment is performed as necessary, so that the secondary coil having a predetermined shape can be obtained.

(3) Step of Inserting Secondary Coil into Shaping Mold

The secondary coil obtained through the step of (2) is inserted into a shaping mold that has an inner hollow section. In the present invention, as described above, the secondary coil to which the shape in which two or more different patterns of two or more kinds are continuously arranged is given is used. The rigidity of the secondary coil varies in the boundary between the different patterns in the secondary coil. Therefore, when the secondary coil is inserted into the shaping mold and thereby makes contact with an inner wall surface that forms the inner hollow section of the shaping mold, it is possible to change the direction of the secondary coil into a random direction in the boundary between the different patterns of the secondary coil. As a result, the secondary coil inserted into the inner hollow section of the shaping mold can move along the entire inner wall surface that forms the inner hollow section. Therefore, it is possible to shape an in-vivo indwelling member having a three-dimensional structure (appearance shape) that corresponds to the shape of the inner hollow section of the shaping mold. The shape of the inner hollow section can be, for example, a shape corresponding to the shape of a bump, specifically, a spherical shape, a generally spherical shape, and the like. However, the shape of the inner hollow section may be other shapes.

An example of the embodiment of the present step will be described with reference to the drawings.

Figure 12:
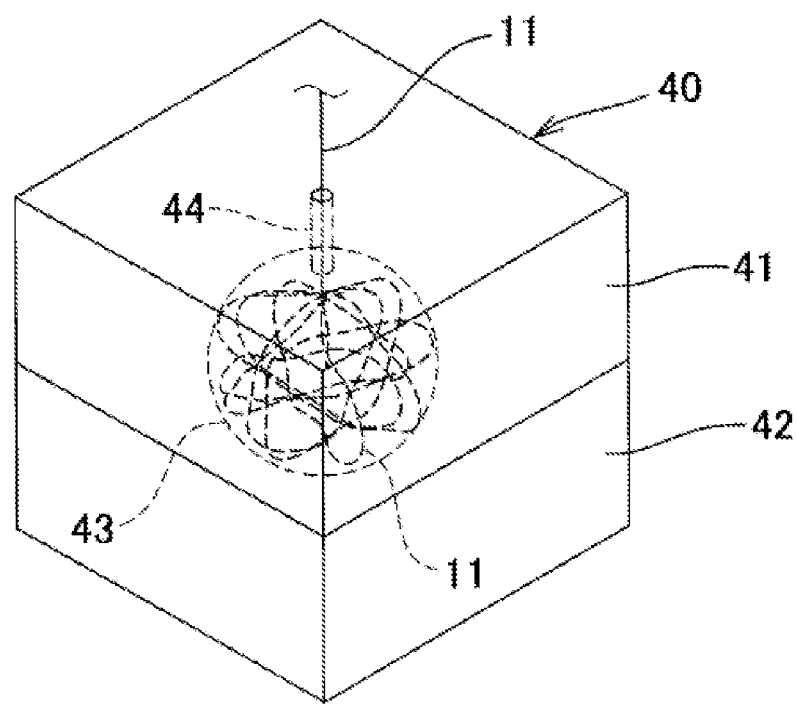
FIG. 12 is a schematic diagram illustrating the shape of an in-vivo indwelling member formed inside a shaping mold in a method for producing an in-vivo indwelling member according to the present invention.

FIG. 12 is an explanatory diagram illustrating a state in the middle of inserting the secondary coil 11 which has the linear pattern 21 and the helical pattern 22 illustrated in FIG. 4(b) into an inner hollow section 43 of a shaping mold 40. In this example, the shaping mold 40 is a split mold which is provided with an upper mold 41 and a lower mold 42. The inner hollow section 43 is generally spherical. A semispherical recess is provided in each of the upper mold 41 and the lower mold 42. When the upper mold 41 and the lower mold 42 are assembled, the generally spherical inner hollow section 43 is formed. The upper mold 41 is provided with a small hole 44 which allows the inner hollow section 43 and the outside to communicate with each other. The secondary coil 11 is inserted into the inner hollow section 43 of the shaping mold 40 through the small hole 44. The inner diameter of the inner hollow section 43 can be appropriately set depending on the size of a bump. For example, the inner diameter of the inner hollow section 43 can be set comparable to or slightly smaller than the outer diameter of the helical pattern 22.

When inserting the secondary coil 11 through the small hole 44, the helical pattern part is inserted while making the helical pattern part linear or in a temporarily linear state. However, the linear shape returns to the helical shape after being inserted into the inner hollow section 43. Then, by inserting the secondary coil 11 into the inner hollow section 43 by a predetermined length, the part of the helical pattern 22 becomes a helical structure along the inner wall surface of the inner hollow section 43 when the helical pattern 22 is comparable to or slightly larger than the inner diameter of the inner hollow section 43. As described above, when the rigidity in the boundary between different patterns varies, the directions of adjacent helical patterns randomly change, and it is therefore possible to change the rotation directions of the helixes of adjacent helical shapes. Accordingly, a large number of helical structures along the inner wall surface of the inner hollow section 43 or deformed structures thereof are more reliably formed. As a result, it is possible to produce an in-vivo indwelling member that has an improved strength and can be stably arranged even when the in-vivo indwelling member has a hollow section.

Also when the inner diameter of the inner hollow section 43 is larger than the outer diameter of the helical pattern 22, directions of adjacent helical patterns randomly change when the rigidity in the boundary between different patterns varies. Therefore, it is possible to produce an in-vivo indwelling member that has an appearance shape corresponding to the structure of the inner hollow section 43 and can be stably arranged.

Figure 11:
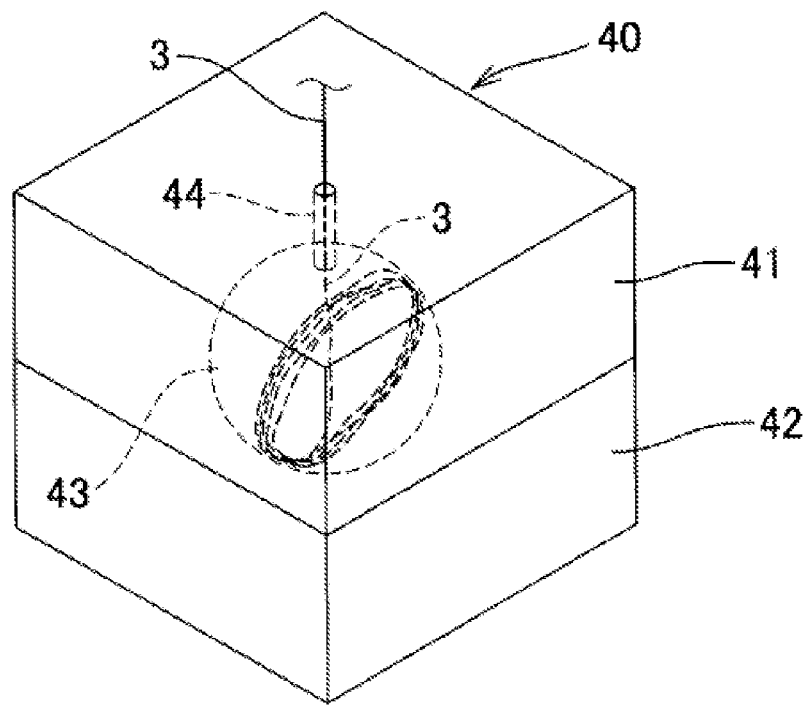
FIG. 11 is a schematic diagram illustrating the shape of an in-vivo indwelling member formed inside a shaping mold in a method for producing an in-vivo indwelling member of a comparative example.

On the other hand, in the case of a conventional method which uses a primary coil 3 illustrated in FIG. 1(b), because the primary coil 3 has only a given shape, even when the primary coil 3 makes contact with the inner wall surface that forms the inner hollow section 43 of the shaping mold 40, the primary coil 3 is merely formed into a shape along substantially the same circumferential part of the inner hollow section 43 as illustrated in FIG. 11. Further, even when heat treatment is performed after inserting the primary coil 3 into the shaping mold 40 as will described below, fixation to its shape cannot be sufficiently performed. As a result, the form after the shaping becomes unstable, and the coil may jump out of a bump after being arranged inside the bump.

As described above, in the present invention, heat treatment can be performed on the shaping mold after the secondary coil is inserted into the inner hollow section of the shaping mold by a predetermined length. Accordingly, the shape that corresponds to the inner hollow section of the shaping mold can be more effectively fixed. Conditions of the heat treatment are not particularly limited. However, when heat treatment is performed in the secondary coil forming step, it is preferred to perform the heat treatment after the insertion at a higher temperature than the temperature in the heat treatment condition in the secondary coil forming step in terms of more effectively fixing the shape formed by the shaping mold, for example, 500 to 900° C. The atmosphere during the heat treatment is the same as that in the secondary coil forming step.

After performing the heat treatment, the shaping mold is cooled. A cooling method is not particularly limited. It is preferred to perform the cooling by a general method, for example, by leaving the shaping mold to stand at room temperature. After the shaping mold is cooled, an in-vivo indwelling member having a three-dimensional structure that corresponds to the structure of the inner hollow section can be obtained from the inside of the shaping mold.

(4) Other Steps

In the present invention, for example, the following steps can be appropriately performed as needed.

(i) Joining of Extension Prevention Wire

When it is necessary to arrange an extension prevention wire inside the primary coil, the extension prevention wire is inserted into the primary coil and connected to the primary coil at a predetermined position after the primary coil forming step as well as around the secondary coil forming step. The material of the extension prevention wire, a method for connecting the wire to the primary coil, and a connection position are not particularly limited. Therefore, a conventional material can be used, and a conventional method and a conventional position can be employed.

As a method for connecting the extension prevention wire after the secondary coil forming step, for example, the following methods can be employed. However, the connection method is not limited to these methods. As a first example, the secondary coil having a predetermined shape is formed, and the obtained secondary coil is thereafter inserted through a linear tube that has an inner diameter slightly larger than the outer diameter of the primary coil so as to be temporarily returned to a linear shape. Then, in the linear state, the extension prevention wire is inserted into the primary coil to thereby connect the end of the extension prevention wire to one end of the primary coil. As a second example, the extension prevention wire is inserted into the primary coil without using the linear tube having an inner diameter slightly larger than the outer diameter of the primary coil used in the first example to thereby connect the end of the extension prevention wire to one end of the primary coil.

(ii) Processing on End of Primary Coil

It is possible to perform processing for providing a semispherical head on one end of the primary coil. The processing can be performed at the same time as the joining of the extension prevention wire in (i). Further, the processing can be performed using another conventional method and material. Further, as necessary, it is possible to join the extension prevention wire and/or a connection member with an arrangement wire (described below) to the other end of the primary coil.

The in-vivo indwelling member obtained in the above manner is joined to the tip of the arrangement wire such as a pusher which has been conventionally generally used, and can thereby be used as a medical device that is used when blocking a bump inside a blood vessel.

EXAMPLE

Hereinbelow, the present invention will be more specifically described on the basis of an example.

Example 1

A metal wire made of a platinum alloy having a wire diameter of ϕ0.045 mm was wound around a linear core metal (core wire) having a substantially constant outer diameter to manufacture a tightly-wound primary coil having an outer diameter of ϕ0.250 mm and an entire length of 300 mm. Then, the core metal was removed.

The primary coil was wound on the mandrel 33 of the jig 30 illustrated in FIG. 6(*a*) (however, the structure having three projections 36) and stopped the winding between the projections 36 (the interval between the projections is approximately 10 mm) to maintain a linear state. Then, the winding was again performed in the same rotation direction as the first winding. The above process was repeatedly performed three times.

Then, in order to fix the shape in the above form, heat treatment was performed at 500° C. for one hour. After the heat treatment, the jig 30 was cooled and then removed to obtain a secondary coil having a generally linear entire shape in which a linear shape (length: approximately 10 mm) and a helical shape (outer diameter: approximately ϕ8 mm, shape: tight winding) are alternately repeatedly arranged.

The secondary coil was temporarily inserted into a linear tube having an inner diameter slightly larger than the outer diameter of the primary coil to thereby temporarily return the shape of a helical part to a linear shape. Then, an extension prevention wire of 0.010 mm was inserted into the primary coil, and the tip of the wire was welded to one end of the primary coil by laser. The secondary coil was inserted into a shaping mold which has a spherical inner hollow section of ϕ8.0 mm with the secondary coil inserted into the linear tube. Then, the shaping mold in which the secondary coil is inserted was heated at 700° C. for one hour to perform heat treatment. Then, the secondary coil was taken out of the shaping mold after cooling to thereby obtain a spherical in-vivo indwelling member having a three-dimensional structure that corresponds to the shape of the inner hollow section of the shaping mold. From the above result, it can be considered that the secondary coil inserted into the inner hollow section of the shaping mold returns to the secondary coil shape having an original helical pattern inside the inner hollow section and the secondary coil is arranged so as to change its direction to various directions inside the inner hollow section.

Comparative Example 1

A primary coil in which an extension prevention wire is arranged was manufactured in the same manner as in Example 1. The primary coil was inserted into the shaping mold used in Example 1. Heat treatment was performed on the shaping mold in which the primary coil is inserted at 700° C. for one hour. The primary coil was taken out of the shaping mold after cooling. As a result, although a helical in-vivo indwelling member in which the primary coil is wound so as to have a substantially constant outer diameter was obtained, the shape thereof was not a spherical shape that corresponds to the shape of the inner hollow section of the shaping mold.

(Evaluation)

The in-vivo indwelling members of Example 1 and Comparative Example 1 were inserted into an aneurysm model made of transparent glass and evaluation thereof was performed.

A microcatheter was inserted into the aneurysm model and the formed shape of the in-vivo indwelling member of each of Example 1 and Comparative Example 1 was released into a linear shape. Then, the in-vivo indwelling member of each of Example 1 and the Comparative Example 1 was arranged inside the aneurysm through the microcatheter. As the result, it was confirmed that, when released from the tip of the catheter, the in-vivo indwelling member of Example 1 returns to the spherical shape and is stably maintained inside the aneurysm. On the other hand, it was revealed that although the in-vivo indwelling member of Comparative Example 1 returns to the helical shape, the possibility of the in-vivo indwelling member jumping out of the aneurysm is not eliminated because the helical shape does not correspond to the shape of the aneurysm.

REFERENCE SIGNS LIST

1 Metal wire
2, 3, 4 Primary coil
5, 10, 11, 12, 13, 14, 15, 16, 17, 18, 19 Secondary coil
6 Interval
7 Wire
20, 22, 23, 24, 25, 29, 61, 63, 64, 65 Helical pattern
21, 26, 28 Linear pattern
27, 50, 51, 52, 53, 60, 62 Circular arc pattern
30, 31, 32, 60 Jig
33, 34, 35, 61 Mandrel
36 Projection
37 Groove
38 Through hole
40 Shaping mold
41 Upper mold
42 Lower mold
43 Inner hollow section
44 Small hole
L Center axis
M, N Center axis
W, W', X, Y, Y', Z Plane
α, β, γ, δ Angle

The invention claimed is:

1. A method for producing an in-vivo indwelling member, the method comprising:
   a primary coil forming step of winding a metal wire to form a primary coil;
   a secondary coil forming step of giving the primary coil a shape in which two or more different patterns of two or more kinds are continuously arranged to form a secondary coil, followed by performing heat treatment; and
   a step of inserting the secondary coil into a shaping mold having an inner hollow section, followed by performing heat treatment at a temperature higher than a temperature of the heat treatment in the secondary coil forming step.

2. The method according to claim 1, wherein the different patterns of two or more kinds include at least one selected from a helical shape, a linear shape, a wavy shape, a curved shape, and a bent shape.

3. The method according to claim 2, wherein the helical shape includes a helical shape having a varying outer diameter.

4. The method according to claim 2 or 3, wherein the inner hollow section of the shaping mold is generally spherical, and a maximum width of the generally spherical inner hollow section is equal to or less than a minimum outer diameter of the helical shape.

5. The method according to claim 1, wherein two of the different patterns of two or more kinds are selected from a curved shape and a helical shape.

6. The method according to claim 2 or 5, wherein the curved shape includes a plurality of circular arc shapes having different curvatures.

7. The method according to claim 6, wherein at least one of the circular arc shapes having different curvatures exists on a plane that differs from a plane on which the other circular arc shapes exist.

8. The method according to claim 5, wherein two of the different patterns of two or more kinds include a circular arc shape and a helical shape that are adjacent to each other, and a center axis of the helical shape is not in a perpendicular relationship with a plane on which the circular arc shape exists.

9. The method according to claim 1, wherein the secondary coil has one or more entire shapes selected from a generally linear shape, a generally wavy shape, a generally spiral shape, and a generally helical shape.

10. The method according to claim 1, wherein a shape in which two or more different patterns of two or more kinds are continuously arranged is given to the primary coil using a processing jig that is in contact with an outer side of the primary coil.

11. The method according to claim 1, wherein a shape in which two or more different patterns of two or more kinds are continuously arranged is given to the primary coil by inserting a shaping wire into the primary coil.

* * * * *